United States Patent [19]

Freezer

[11] 4,083,368
[45] Apr. 11, 1978

[54] INHALER

[76] Inventor: Winthrop J. Freezer, 1141 Folsom Street, Paris, France, 94103

[21] Appl. No.: 719,546

[22] Filed: Sep. 1, 1976

[51] Int. Cl.² .......................................... A61M 15/08
[52] U.S. Cl. ................................... 128/198; 128/206
[58] Field of Search .................. 128/198, 173 R, 186, 128/188, 194, 195, 199, 200, 201, 205, 206, 207, 208, 209, 210, 140 N, 239, 240, 247, 184

[56] References Cited

U.S. PATENT DOCUMENTS

| | | | |
|---|---|---|---|
| 2,427,721 | 9/1947 | Goldstein | 128/198 |
| 2,448,803 | 9/1948 | Hunter | 128/239 |
| 2,672,865 | 3/1954 | Willis | 128/206 |
| 3,255,750 | 6/1966 | Schwartzman et al. | 128/198 |

FOREIGN PATENT DOCUMENTS 512,158   4/1955   Canada ............................... 128/198

Primary Examiner—Robert W. Michell
Assistant Examiner—Henry J. Recla
Attorney, Agent, or Firm—Townsend and Townsend

[57] ABSTRACT

A nasal inhaler having paired spaced apart inhalant dispensing cylindrical passageways is disclosed. The inhaler includes a base portion with paired concavities for receiving inhalant compounds. These concavities each receive overlying paired nasal cylinders. These overlying paired nasal cylinders each terminate at spherical endings adapted for simultaneous reception into the nostrils. Each cylinder has two apertures: one, axially of the cylinder at the spherical end for dispensing inhalant vaporized air; the second aperture in the cylinder sidewall for taking in air for inhalant vaporization. When the inhaler is not in use, a cap having paired apertures for fitting freely over each of the inhalant dispensing cylinders is placed over the cylinders. This cap confronts the inhaler base, preferably at polypropylene gaskets surrounding each nasal cylinder where the top seals both nasal cylinders. This cap is fastened medially between the nasal cylinders to the base by a bolt which clamps the top firmly onto the washers about each nasal cylinder. As a result, inhalant compounds can be stored for long periods of time without leakage while the inhaler is not in use.

9 Claims, 3 Drawing Figures

U.S. Patent  April 11, 1978  4,083,368
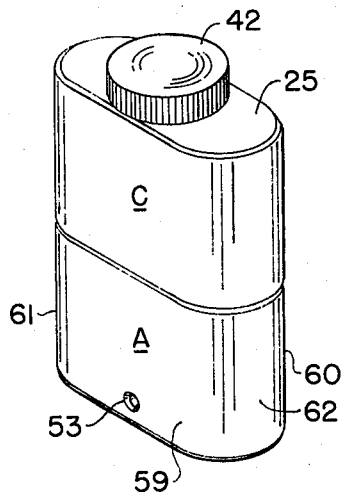
FIG.__1.
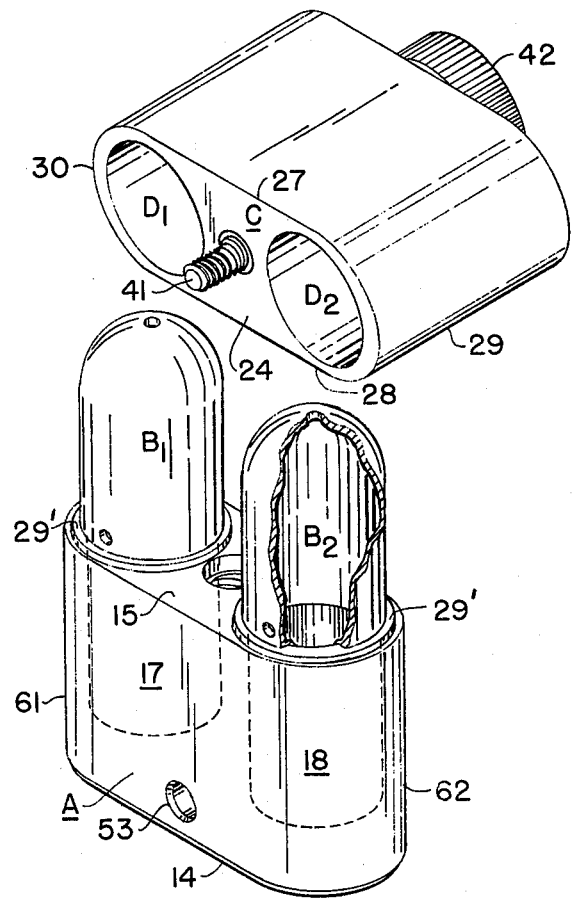
FIG.__2.
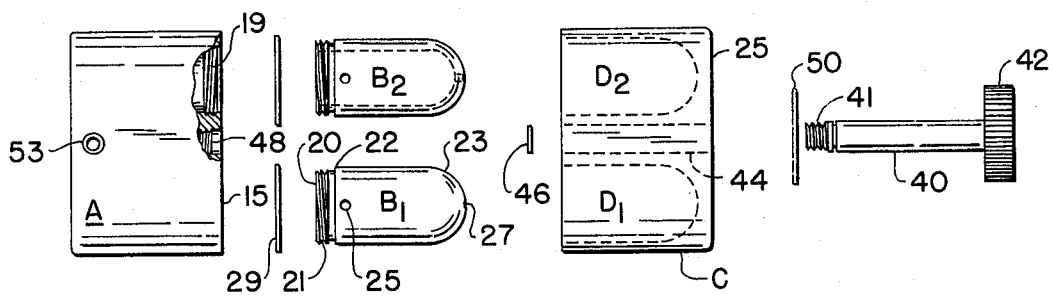
FIG.__3.

INHALER

This invention relates to inhalers. Specifically, this invention relates to a dual inhaler.

SUMMARY OF THE PRIOR ART

Dual inhalers are known. However, the sealing of such dual inhalers in a pocket size configuration has heretofore constituted a problem. This problem is especially critical where inhalers are used to dispense needed medicants (for instance, amyl nitrite or nitrogylcerin to heart patients). Commonly, such patients only need inhalers occasionally, but when they are needed their use is critical. If such inhalers have leaked their inserted medicant to atmosphere and are no longer charged, the attended results can be catastrophic for the patient.

SUMMARY OF THE INVENTION

A nasal inhaler having paired spaced apart inhalant dispensing cylindrical passageways is disclosed. The inhaler includes a base portion with paired concavities for receiving inhalant compounds. These concavities each receive overlying paired nasal cylinders. These overlying paired nasal cylinders each terminate at spherical endings adapted for simultaneous reception into the nostrils. Each cylinder has two apertures: one, axially of the cylinder at the spherical end for dispensing inhalant vaporized air; the second aperture in the cylinder sidewall for taking in air for inhalant vaporization. When the inhaler is not in use, a cap having paired apertures for fitting freely over each of the inhalant dispensing cylinders is placed over the cylinders. This cap confronts the inhaler base, preferably at polypropylene gaskets surrounding each nasal cylinder where the top seals both nasal cylinders. This cap is fastened medially between the nasal cylinders to the base by a bolt which clamps the top firmly onto the washers about each nasal cylinder. As a result, inhalant compounds can be stored for long periods of time without leakage while the inhaler is not in use.

OBJECTS AND ADVANTAGES OF THE INVENTION

It is an object of this invention to design a dual inhaler which can be sealed for long periods of time. Accordingly, the inhaler is provided with two confronting sections: one, a medicant receiving section; the other, a cap section. On the medicant receiving section, there are extending paired inhalant dispensing cylinders. These cylinders fit within the cap section and have surrounding their base a large propylene washer. The cap section is locked to the medicant section by a central screw which extends between dispensing cylinders.

An advantage of the single screw fastening of the cap section between the dispensing cylinders is that the cap is drawn in firm sealing relation over each of the medicant dispensing cylinders. An absolutely airtight seal of medicant results.

A further advantage of the single screw fastening of the cap is that the cap is capable of one-handed opening or closing by the user. Handling of the inhaler by both hands is not required. Moreover, such opening or closing is swift, positive, and does not require inordinate attention to the cap manipulation.

A further advantage of this invention is that inhalant compounds can be maintained for extremely long periods of time in the inhaler without loss of the inhalant compound.

Yet a further advantage of this invention is that the dual inhaler is a relatively thin object capable of being carried in the pocket of the user. When it is continually carried in the pocket of the user, it rapidly absorbs body heat and is in a state where vapors can be immediately released upon use.

Still another advantage of this invention is that an inhaler is disclosed which can be loaded at convenience by the consumer or the consumer's pharmacist. Moreover, this loading can be repeated without interfering with either the construction or operation of the inhaler. Thus, an inhaler is disclosed which is readily adapted to prescribed and/or individually necessary drugs.

Other objects, features and advantages of this invention will become more apparent after referring to the following specification and attached drawings in which:

FIG. 1 is a perspective view of the inhaler in the sealed disposition;

FIG. 2 is a front elevation perspective of the inhaler bottom and paired nasal cylinders with the inhaler top shown overlying the bottom in a perspective view; and, FIG. 3 is an exploded side elevation view in partial section of the inhaler illustrating its component parts.

Referring to all the figures, the construction of the inhaler can be described. The base A of the inhaler is typically annodized aluminum. When viewed in front elevation it includes a flat bottom 14 and a flat top surface 15. Base A includes two flat parallel and spaced apart sidewalls 59, 60. These sidewalls are connected by semicircular sidewall portions 61, 62.

Base A defines interiorly thereof two inhalant compound receiving concavities 17, 18. Each of these inhalant compound receiving concavities is provided with female threads 19 at the upper end. These threads provide for attachment of the paired nasal cylinders $B_1$, $B_2$ overlying each of the inhalant compound receiving concavities 17, 18.

Referring to FIG. 3, the construction of the nasal cylinders can be easily understood. Typically, the cylinders are each hollow and opened at a circular and lower end 20. At the opening, the cylinders are each threaded with male threads 21 and provided with an overlying shoulder 22. The cylinders $B_1$, $B_2$, extend upwardly from the shoulder 22 and terminate in a substantially spherical ending 23. Air to be vaporized with the inhalant compound flows into each cylinder at a sidewall aperture 25 in the sidewall of the cylinders $B_1$, $B_2$. After entrance into the cylinder and passage around, through and within the compound receiving concavity, this air flows out of the cylinder at the spherically closed upper end through a central aperture 27. Preferably the inhalant compound is disposed within a wick as is well known in the art.

The cylinders $B_1$, $B_2$ fasten to female threads 19 on base A with a polypropylene 29' between the cylinder shoulder 22 and top 15 of base A. As will hereinafter be more fully set forth, each of the 29' extends radially beyond nasal cylinders $B_1$, $B_2$ to provide a sealing surface against which top C can bear.

Assembly of the base A of the inhaler can be easily understood. Each of the 29' is placed overlying one of the inhalant compound receiving concavities 17, 18 with the inhalent compound previously placed within the cavities. Thereafter, each one of the cylinders $B_1$ and $B_2$ is threaded onwardly to the bottom portion A.

The top C is provided with paired cylindrical apertures $D_1$, $D_2$. Apertures $D_1$, $D_2$ are cylindrical and sized to freely fit over nasal cylinders $B_1$, $B_2$.

Top C includes a flat bottom surface 24, a flat upper surface 25, and like base A is typically constructed of annodized aluminum. Similar to bottom portion A, the cap includes two flattened sidewall portions 27, 28 connected by semi-cylindrical sidewalls 29, 30. In cross-section walls 27–30 of top C are all the same dimension as the corresponding cross-section of walls 59-62 of base A.

It will be remembered that each of the 29' has an outer dimension whereby 29' are extended beyond the sidewalls of the nasal cylinders $B_1$, $B_2$. When the top C is placed in confronting relation over nasal cylinders $B_1$, $B_2$, and firmly fastened down onto the bottom portion A, 29' confront the flat bottom surface 24 of the top. In this confrontation, the flat bottom surface 24 bears upon 29' firmly. This bearing seals each of the cylinders $B_1$, $B_2$ interior of the apertures $D_1$, $D_2$ in the top.

It should be noted that when top C fits over bottom A, both apertures of the inhalant cylinders are firmly sealed. That is to say, the cap simultaneously covers the central apertures 27 as well as the sidewall apertures 25 of each of the nasal cylinders $B_1$, $B_2$.

Sealing force to top C is provided by a bolt 40 having a threaded end 41 and a knurled knob 42. Knob 42 fits axially of a complementary central aperture 44 extending entirely through top member C medially between cylinder receiving apertures $D_1$, $D_2$. Typically, bolt 40 is fastened onto and is free to rotate within top C by a locking washer 46.

In operation, cap C is placed overlying each of the nasal cylinders $B_1$, $B_2$. Threaded portion 41 is entered into threads 48 in base A. By turning of the knurled knob 42, the top is entered and firmly held in sealing relation over each of the inhalant dispensing cylinders $B_1$, $B_2$.

It should be noted that the sealing of this invention is simply and easily accomplished. First, apertures $D_1$, $D_2$ in top C fit over cylinders $B_1$, $B_2$. This fit over cylinders $B_1$, $B_2$ prevents the rotation of the top about the bolt 40 when top C is fastened over base A. Secondly, as the bolt 40 is medially placed between the paired nasal cylinders $B_1$, $B_2$, the cap is drawn over both cylinders with a uniform force. It sits firmly and on top of each of the 29' effecting a positive airtight seal. Moreover, and due to a polypropylene washer 50 between knurled knob 42 and the upper surface 25 of the top portion of the inhaler, knob 42 and bolt 40 are easily rotated. This ease of rotation provides high leverage effecting the seal of top C over base A. A firm, long-lasting seal of inhalant compounds within the inhalant receiving concavities 17, 18 results.

It should be understood that the function of polypropylene washer 50 is to provide a high lubricity membrane between knob 42 and top C. With a high lubricity membrane, ease of rotation of bolt 40 provides improved purchase to the force of the positive seal of cap C.

It will further be appreciated that 29' assist the sealing of the nasal cylinders $B_1$, $B_2$ in two ways. First, when the cylinders $B_1$, $B_2$ are screwed on base A, the nasal cylinders are each sealed onto the base at the 29'. All air flow into and out of the cylinders must occur through apertures 25, 27.

Secondly, and when top C is fastened over base A, 29' furnish the seal between the top at cavities $D_1$, $D_2$ and respective nasal cylinders $B_1$, $B_2$.

It will be appreciated that the inhaler of this invention is designed for preferred use with needed medicants (such as amyl nitrite or nitroglycerin for heart patients). There is provided for the convenience of the user an aperture 53 through the bottom portion A. Aperture 53 transpierces the bottom portion A and provides a convenient place for the threading of a string, chain or the like so that the inhalant can be fastened securely for transport by the user.

It should be appreciated that the invention herein will admit of modification. For example, the inhaler could be fabricated of numerous materials including plastics and the like. Further, either the top C or base A could communicate at their apertures to single concavities in the top and base. Additionally, although the preferred embodiment discloses paired confronting flat surfaces 15 on base A and 24 on cap C, it is not required that these surfaces be flat. So long as the surfaces confront to provide an uninterrupted sealing interface between the cap and base at the nasal cylinders, the parameters of the invention are base at the nasal cylinders, the parameters of the invention are met. Likewise, other modifications can be made so long as the seal of this invention is maintained.

I claim:

1. A nasal inhaler having two (paired) spaced apart inhalant dispensing cylindrical passageways comprising: a base, said base having a surface with two (paired) apertures defined through said surface into at least one concavity in said base, said concavity for receiving inhalant compounds; two (paired) nasal cylinders, each said cylinder terminating at one end in a substantially spherical end and open at the opposite end to the concavity, said nasal cylinders each provided at said opposite end with means for attachment to said base overlying one of said two (paired) apertures; each said nasal cylinder including first and second openings, one of said openings disposed substantially axially of said cylinder at said spherical end for dispensing inhalant vaporized air from within said inhalant receiving concavity, and a second opening in the cylinder sidewall for taking in air for inhalant vaporization; a cap, said cap defining a surface complimentary to the surface of said base to provide a substantially uninterrupted sealing interface about said cylinders; at least one aperture (paired apertures) for freely fitting over each of said inhalant dispensing cylinders extending through said surface and extending into at least one concavity defined within said cap for receiving the nasal cylinders whereby when said surface of said cap is confronted to the surface of said base, (top) said nasal cylinders are each sealed at both said openings within said cap; at least one gasket extending peripherally about each of said nasal cylinders overlying the surface of said base, said gasket confronted by the surface of said cap for sealing said nasal cylinders within said cap said gasket at a first portions captured between said nasal cylinders and said surface of said base, and said gasket at second and outer portions are captured between the surface of said base, and the surface of said cap when said cap at the surface of said cap confronts the surface of said base with said gaskets there between; and, means for confronting under compression at said surfaces said cap (top) to said base on said cap for positive sealing of inhalants within said inhaler.

2. The invention of claim 1 and wherein said means for confronting on said cap includes a bolt, an aperture in said cap extending between said paired apertures of said cap for rotatably mounting said bolt, and a threaded connection at the bottom of said bolt proximate to said surface for threaded connection to said base, and a complimentary threaded aperture in said base underlying said threaded connection of said bolt to permit said bolt to penetrate said threaded aperture of said base and transmit to said cap compression to said base.

3. The invention of claim 1 and wherein said base defines paired concavities, each concavity communicating to one of said apertures defined through said surface.

4. The invention of claim 1 and wherein said defines paired concavities, each concavity communicating to one of said paired apertures.

5. The invention of claim 1 and wherein said cap and base surfaces are each flat.

6. In a nasal inhaler having a base, two (paired) nasal cylinders extending upwardly from said base, said cylinders provided with first openings for dispensing inhalant vaporized air disposed axially of said cylinders at one end thereof and a second opening in the cylinder sidewall adjacent an opposite end thereof for taking in air for inhalant vaporized air from within said inhalant receiving concavity and a cap extending over said two (paired) nasal cylinders for sealing said cylinders when said inhaler is not in use, the improvements comprising: a surface defined in said base with two apertures defined through said surface extending into at least one concavity in said base, said concavity for receiving inhalant compounds; means on said two (paired) nasal cylinders and on said base for fastening said nasal cylinders to said base; a surface on said cap complimentary to the surface of said base to provide a substantially uninterrupted sealing interface about said cylinders; at least one (paired) aperture defined in said cap for freely fitting over each of said inhalant dispensing cylinders, said apertures extending through said surface and extending into at least one concavity defined within said cap for receiving said nasal cylinders whereby when the surface of said cap (top) is confronted to the surface of said base, said nasal cylinders are sealed within said cap (top); and, means for confronting under compression said cap to said base includes a bolt and knob attached to said bolt; a friction reducing membrane between said knob and bolt for providing high lubricity rotation of said bolt with respect to said cap; an aperture extending axially of said cap having a threaded portion of said bolt extending through the surface of said cap; said base defining a complimentary threaded aperture; upon rotation of said knob, said cap is urged to seal said base and said two nasal cylinders at said confronted surfaces of said cap and base.

7. A nasal inhaler having two spaced apart inhalant dispensing cylindrical passage ways comprising: first and second confronting members, said first member comprising a base defining along one side thereof a planar surface with two apertures defined through said surface extending into at least one concavity in said base, said concavity for receiving inhalant compounds; two nasal cylinders, each said cylinder terminating at one end and open at the opposite end to the concavity, said nasal cylinders each provided at said opposite end with means for attachment to said base overlying one of said two apertures; each said nasal cylinder including first and second openings, one of said openings disposed substantially axially of said cylinder at said one end for dispensing inhalant vaporized air from within said inhalant receiving concavity, and a second opening in the cylindrical sidewall adjacent said opposite end for taking in air for inhalant vaporization; said second member comprising a cap, said cap finding a planar surface complimentary to said surface of said base to provide a substantially uninterrupted sealing interface about said cylinder; at least one aperture for freely fitting over each of said inhalant dispensing cylinders extending through said surface of said cap and extending into at least one concavity defined within said cap, said surface of said cap when confronted at the planar surface of said base providing a sealing surface whereby said nasal cylinders are each sealed at both said openings within the concavity of said cap; means for confronting under compression said cap to said base including a bolt and knob attached to said bolt; a friction reducing membrane between said knob and bolt for providing high lubricity rotation of said bolt from one of said members to the other of said members; an aperture extending axially through one of said members, said bolt extending through said aperture and extending beyond the said surface of said one member; a complimentary threaded aperture in the others of said members said bolt threadedly engaged in said threaded aperture whereby upon rotation of said knob, said cap and base are urged to seal across their respective confronted planar surfaces and said two nasal cylinders are sealed within the concavity defined within said cap.

8. The invention of claim 7 wherein said knob and bolt are attached to said cap.

9. The invention of claim 7 and including at least one gasket extending peripherially about each of said nasal cylinders overlying the planar surface of said base, said gasket confronted by the surface of said cap for sealing said nasal cylinder within said cap.

* * * * *